United States Patent [19]

Marquiss

[11] Patent Number: 4,846,003
[45] Date of Patent: Jul. 11, 1989

[54] ACOUSTIC IMPEDANCE SYSTEM FOR PIPETTE TIP DETECTION

[75] Inventor: Samuel A. Marquiss, Santa Clara, Calif.

[73] Assignee: Beckman Instruments, Inc., Fullerton, Calif.

[21] Appl. No.: 204,592

[22] Filed: Jun. 8, 1988

[51] Int. Cl.[4] .............................................. B01L 3/02
[52] U.S. Cl. .................................................. 73/864.24
[58] Field of Search ............ 73/863.01, 864.23, 864.24, 73/864.11, 864.13, 290 V, 290 R; 367/908; 422/100; 340/618, 621

[56] References Cited

U.S. PATENT DOCUMENTS

| | | | |
|---|---|---|---|
| 3,474,902 | 10/1969 | Putman | 73/290 R |
| 4,228,831 | 10/1980 | Kerns | 422/100 |
| 4,341,736 | 7/1982 | Drbal et al. | 422/100 |
| 4,478,094 | 10/1984 | Salamaa et al. | 422/100 |
| 4,715,413 | 12/1987 | Backlund et al. | 73/864.24 |
| 4,790,183 | 12/1988 | Pfost et al. | 367/908 |

FOREIGN PATENT DOCUMENTS

| | | | |
|---|---|---|---|
| 0164957 | 12/1981 | Japan | 422/100 |
| 0777450 | 12/1980 | U.S.S.R. | 73/290 V |
| 2177510 | 1/1987 | United Kingdom | 73/290 V |

*Primary Examiner*—Stewart J. Levy
*Assistant Examiner*—Robert R. Raevis
*Attorney, Agent, or Firm*—William H. May; P. R. Harder; Thos. Schneck

[57] ABSTRACT

A measuring system for use with automated pipettes for determining the presence or absence of a pipette tip. The central conduit of the pipette is connected to a source of pressure waves, such as a speaker and also connected to a pressure wave detector, such as a microphone. Changes in acoustic impedance between an open conduit when no tip is present, a partially constricted conduit when a tip is present, and a closed conduit when the liquid boundary layer is contacted determine the measured states of the apparatus.

16 Claims, 3 Drawing Sheets

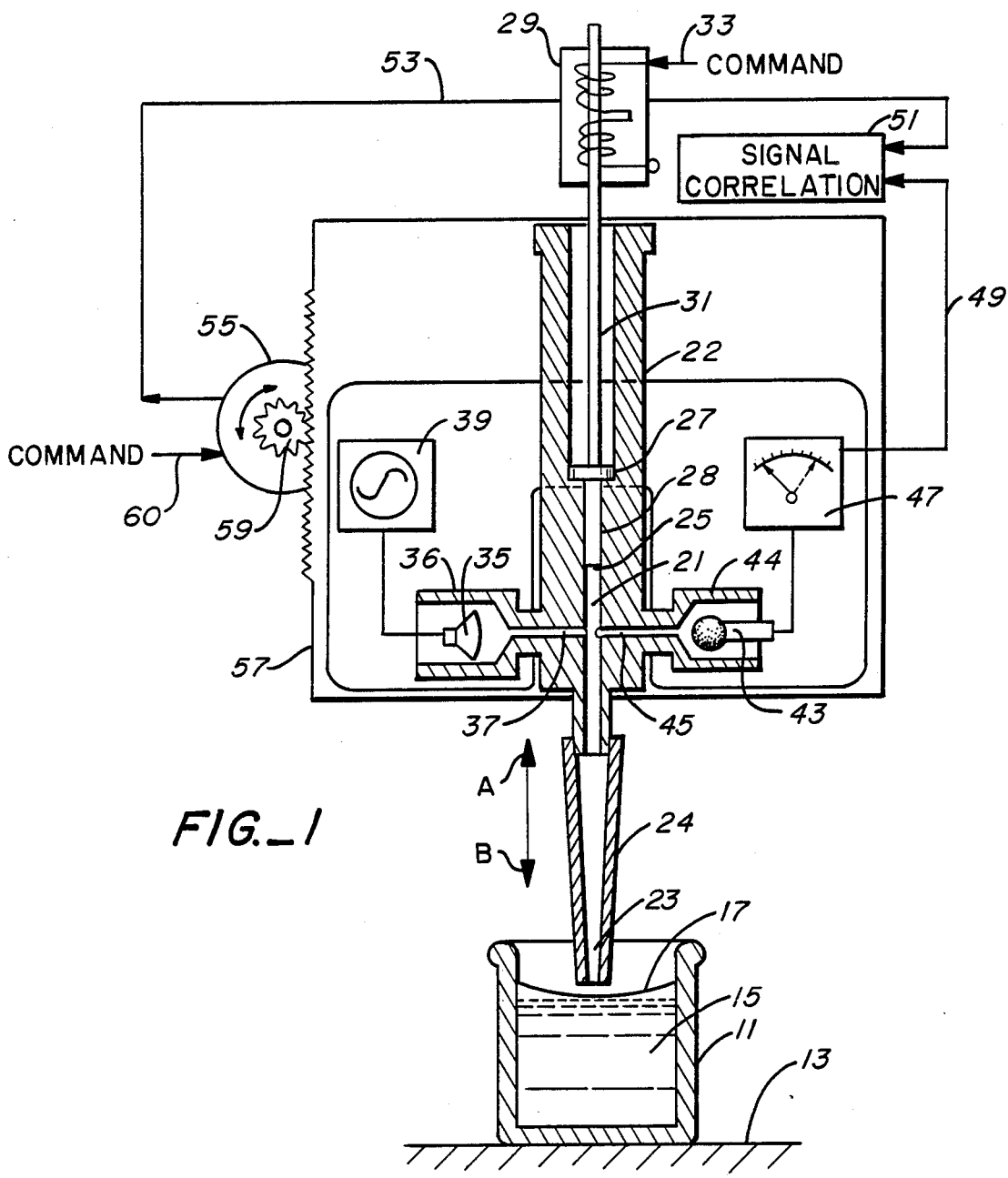
FIG._1
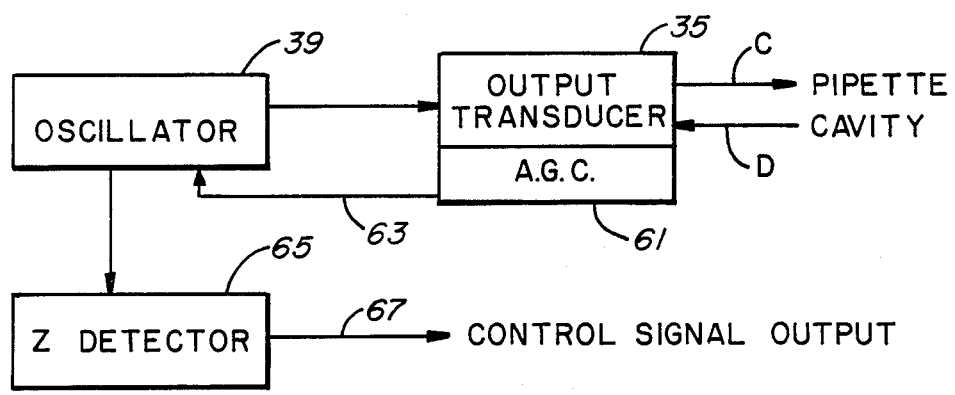
FIG._2

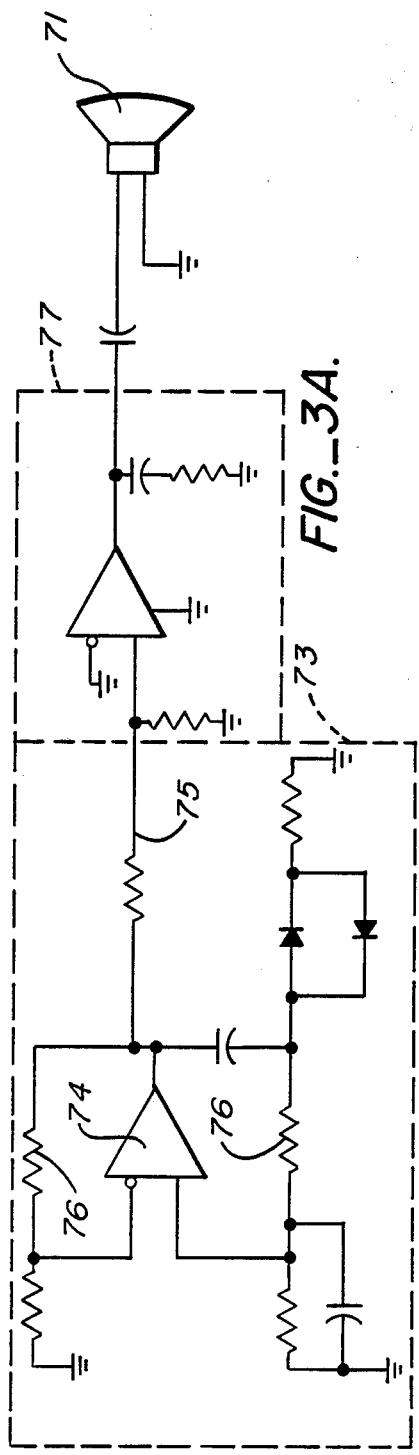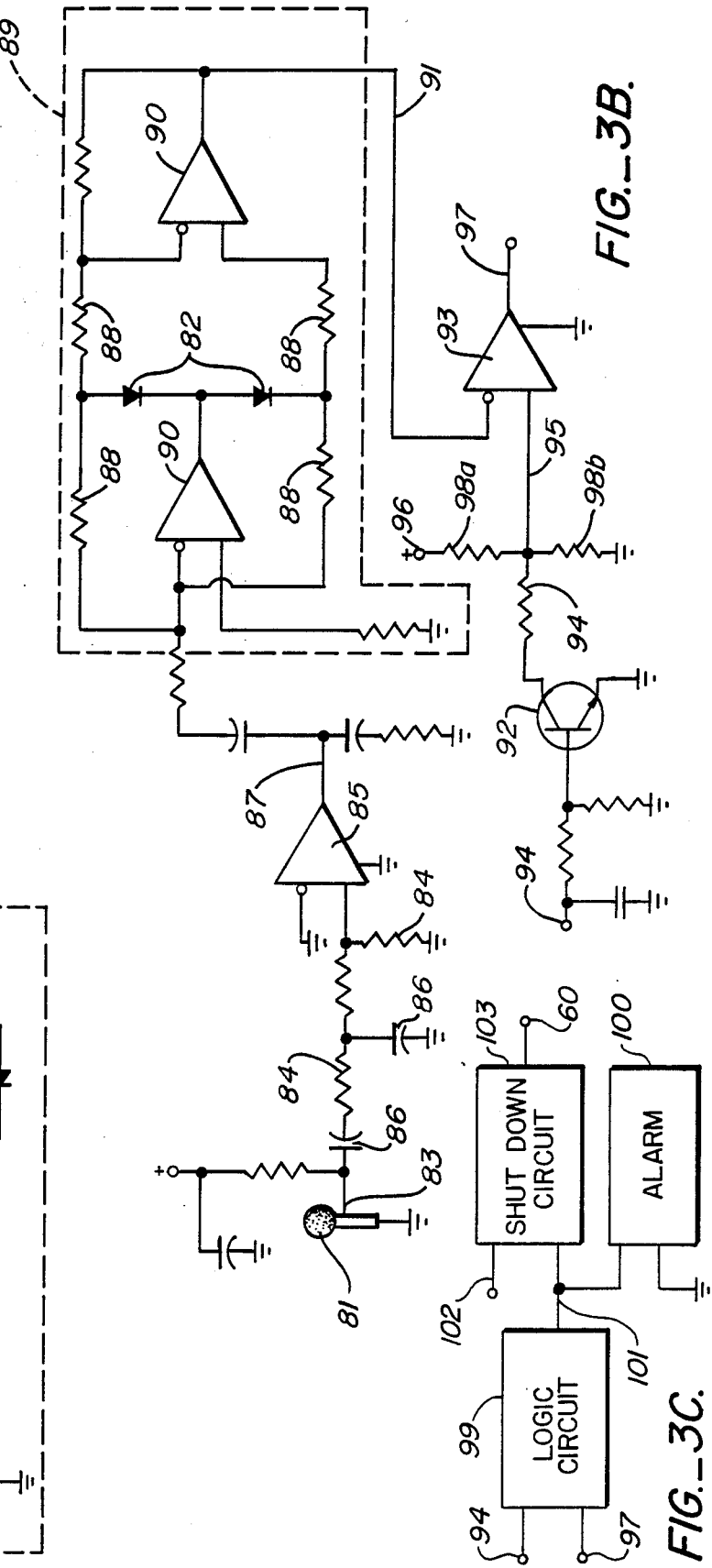
FIG._3A.
FIG._3B.
FIG._3C.

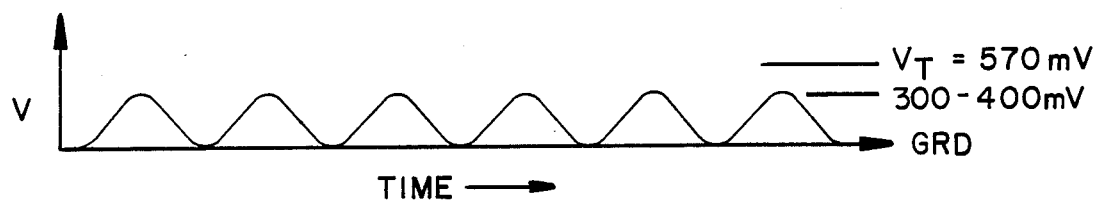
FIG._4A
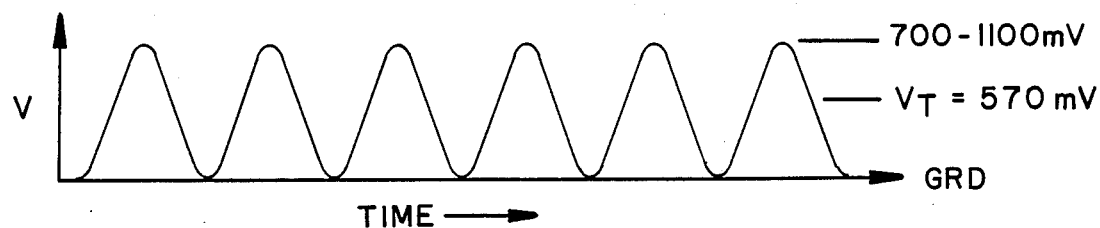
FIG._4B
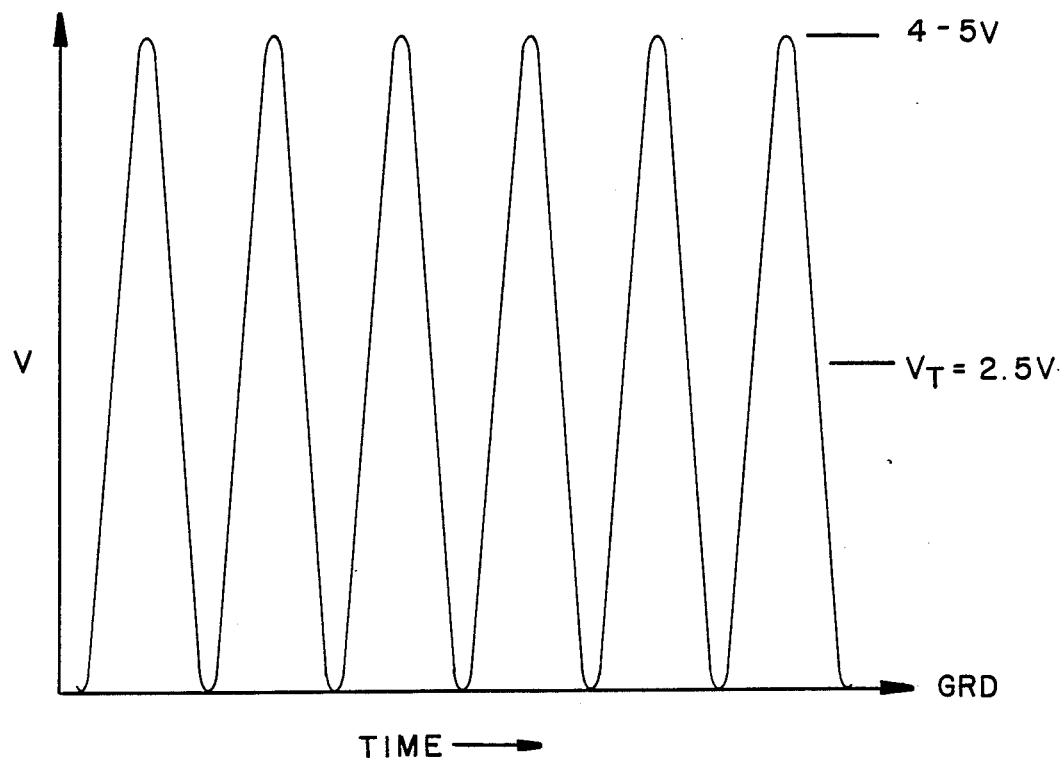
FIG._4C

ACOUSTIC IMPEDANCE SYSTEM FOR PIPETTE TIP DETECTION

DESCRIPTION

1. Technical Field

The invention relates to apparatus for detecting presence or absence of a tip in an automated pipette.

2. Background Art

In prior application Ser. No. 047,043 a system is disclosed for detecting liquid boundaries by means of changes in acoustic impedance in a hollow conduit between a first level when the conduit is open and a second level when the conduit is closed. The apparatus features a means for moving the conduit into contact with a liquid boundary for establishing the liquid boundary level. A change in acoustic impedance upon liquid boundary contact is correlated with a signal indicative of the conduit position to establish the position of the liquid boundary. The conduit may have a pipette tip or the like attached or may be free of a tip.

The presence or absence of a tip is important for automated pipettes because the absence of a tip can lead to contamination of the main conduit tube. Even small quantities of a hazardous substance may cause uncertainties regarding the chemical purity or sterility of the principal pipette conduit. If such uncertainties were to arise, either an automated pipettor would have to be replaced, or at least sterilized, with a substantial loss of time and effort.

An object of the present invention was to devise apparatus for determining whether a pipette tip is attached to an automated pipettor.

SUMMARY OF INVENTION

In music, it is known that there is a substantial change in vibrational modes between an open organ pipe and a closed one. If both ends of a pipe or conduit are closed, and acoustic waves are introduced, the waves must be reflected from the closed ends, known as nodes. An open end, on the other hand, has no such restriction and is known as an anti-node. Intermediate constrictions between the ends are also known to affect the nodes. The present invention relies upon the establishment of acoustic vibrations in an open ended conduit, i.e. one having an anti-node, and then detecting a change in acoustic impedance when the anti-node is affected by a liquid boundary which closes the open end of the conduit, or by constriction of the conduit indicative of whether a tip is attached to the conduit or the conduit is open.

Pressure waves are introduced into a conduit by means of a hollow tube leading into a side wall of the conduit. When an open ended conduit is moved into a liquid boundary, the amplitude or wavelength or frequency or phase of the acoustic waves changes, i.e. there is a significant characteristic change in acoustic impedance, and this change may be detected with an electrical circuit. When the conduit is partially constricted, as by a tip, there is less of a change in the signal, but still a distinctive characteristic exists. Thus, the apparatus recognizes three conditions: (1) no tip attached; (2) tip attached but clear of liquid boundary; (3) tip attached and contact made with fluid boundary. The waves which are used in the conduit are continuous waves, not of the pulse-echo type. Once the change in acoustic impedance occurs, contact with a liquid boundary is established. By monitoring changes in the relative position of the conduit when contact with the liquid boundary is established, changes in height of the liquid boundary are monitored.

BRIEF DESCRIPTION OF THE DRAWINGS

FIG. 1 is a side plan view of the apparatus of the present invention.

FIG. 2 is a simplified electrical schematic for a single transducer embodiment of detection circuits employed with the apparatus of FIG. 1.

FIGS. 3A and 3B are detailed electrical schematics of a two transducer version of the circuits of FIG. 2.

FIG. 3C is a detailed electrical schematic of an alarm and shut-off circuit employed with the apparatus of FIG. 1.

FIGS. 4A-4C show three signal plots indicating three tip conditions in the apparatus of FIG. 1.

BEST MODE FOR CARRYING OUT THE INVENTION

With reference to FIG. 1, container 11 is shown resting on surface 13 in a known position. The container 11 may be a cuvette, vial, beaker or other liquid sample container. The container need not be a laboratory container, but may be a large industrial chemical process tank. The container contains a liquid 15 to be dispensed or handled. A liquid boundary layer 17 defines the upper surface of the liquid, separating it from air or any ambient gas.

The liquid handling apparatus employed in the present invention includes an open-ended conduit 21 which is preferably an automated pipette of a type similar to that described in the above mentioned patents. The conduit has an open end 23 and an opposite end 25 closed by a plunger 27 which may be operated by an electrical actuator 29. A removable tip 24 is frequently used at the end of a pipette, but this is optional for the invention. The plunger 27 has a movable end 28 in sealed relation to the interior wall of conduit 21.

The purpose of the plunger 27 is to draw or expel a liquid specimen from or into the conduit 21, to a desired extent, for transfer to another container or laboratory receptacle. The plunger is connected by a rod 31 to actuator 29, which may be a stepping motor or a linear motor or magnetostrictive actuator. In all cases, the actuator responds to command signals entered on electrical line 33, moving a plunger 27 up and down to the desired extent. If very fine motion is desired, actuator 29 may be servo controlled.

Air displacement waves, such as acoustic waves are established in conduit 21. This may be achieved by an acoustic transducer, such as a miniature speaker 35 emitting pressure waves into a first hollow tube 37 which penetrates the side wall of conduit 21, thereby communicating pressure waves from the speaker into the conduit. The pressure waves are preferably acoustic waves, although non-sonic waves may also be used.

It is known that an open pipe has a natural or resonant frequency which is twice that of a closed pipe. Of course, waves introduced into the conduit are not necessarily of a resonant frequency. However, wave behavior is similar to the physics of pipes because when the conduit is closed, by contact of tip 24, with the liquid interface 17, nodes exist at opposite ends of the conduit forcing a certain vibrational mode. This vibrational mode creates a characteristic acoustic impedance which is quite different from the situation where the conduit is open. Acoustic impedance may be measured by changes in amplitude of waves within the conduit, changes in frequency, phase or measurement of the change in the quality factor, Q, of the transducer causing the vibrations. The quality factor, Q, is a measure of the loading or losses in the conduit by the excitation transducer or wave transmitter with respect to the opened or closed conduit end. Measurement of loading is a direct measurement of acoustic impedance.

An electrical sine wave oscillator 39 provides electrical excitation to the speaker 35 which acts as a pressure wave transducer. The pressure wave output frequency has no limits. Loading of the speaker 35 may be measured by a circuit having a feedback feature, such as an automatic gain control circuit, with the objective of maintaining a certain output level to the conduit. When the conduit is closed by contact with the liquid boundary, or is partially closed by the presence of a pipette tip, partially constricting the conduit opening, there will be a need for a change in speaker output to maintain a constant pressure wave amplitude level in conduit 21. This is sensed at the speaker 35 and a feedback signal may be sent to oscillator 39 to change its wave amplitude to maintain the desired level in the conduit. On the other hand, when the conduit is completely open, a different amount of work needs to be done by the speaker and so the amount of corrective feedback to the oscillator is changed.

Another means for sensing the pressure wave condition in conduit 21 is by means of a microphone 43 which communicates with conduit 21 by means of a second hollow tube 45 which penetrates the side wall of conduit 21, preferably opposite the first tube 37. Microphone 43 senses pressure waves in conduit 21, but preferably not directly to tube 37. In other words, the first and second tubes must be spaced in a manner such that pressure waves are communicated throughout the cavity not merely going directly from speaker 35 to microphone 43, but interact first in the conduit 21. Microphone 43 has an electrical output which is connected to a detector 47 which is able to measure signal level and produce an output along line 49. While the detector is indicated to be an optically read analog meter, this is only schematic. The detector is read electrically and may be an analog or digital circuit. The detector output along line 49 is fed to a signal correlation circuit 51 which correlates the detected signal to a position signal arriving along line 53 from a positioning motor 55. For example, if motor 55 is a stepper motor, each step or motor pulse represents an amount of displacement from a starting point. If the starting point of the conduit tip is known relative to reference surface 13, tip advancement can be measured to the point of impingement with the liquid boundary layer. This measurement is carried out by correlation circuit 51 and yields liquid level or height with respect to the reference surface. However, in most instances absolute starting points are not known, but once the liquid level is detected, all other positions can be related to this. Thus it is not essential to know the position of a reference surface.

Conduit 21 is formed as a bore in a cylinder 22 which is only 5-15 centimeters long with a diameter of 13 centimeters. Tubes 37 and 45 are also formed as bores in the same metal body, although they could be removable tubes. Speaker 35 and microphone 43 are both miniature components, only a few millimeters in size, which are removably placed into respective housings 36 and 44 forming enlarged ends of tubes 37 and 45. The dimensions mentioned herein are only exemplary. The pressure waves need not be generated by an electrical oscillator, but may be generated by mechanical motion of the conduit. For example, a stepper motor may generate pressure waves in moving the conduit toward a liquid level.

The liquid handling apparatus described above is mounted in a housing 57 which may be moved up and down as indicated in the direction of arrows A-B, by means of gear 59 or outer linear positioning mechanism. Housing 57 also supports oscillator 39 and detector 47 on small cards. Motor 55 may be commanded by a command signal 61 to move up or down, incrementally, by a desired amount. For very fine positioning requirements, a servo may be employed.

When a change in acoustic impedance occurs, a conduit obstruction is indicated. A partial obstruction indicates tip presence and a complete obstruction indicates that the level of a liquid boundary layer has been determined. It is not necessary to measure the conduit's vertical position as long as the extent of its motion is known relative to a reference liquid boundary position.

Motor 55 moves the tip 24 into contact with the liquid boundary 17. Since oscillator 39 is on continuously, a significant change in acoustic impedance within conduit 21, as measured by a detector, may be instantaneously correlated in signal correlator 51 with the vertical position of housing 57. This measurement of liquid level may be correlated with previous measurements for monitoring change in liquid level or volume.

With reference to FIG. 2, the output transducer 35, emitting pressure waves indicated by arrow C, also acts as a sensor of acoustic impedance. This is indicated schematically by arrow D wherein the loading of the output transducer may be sensed in different ways. One feedback method is by means of an automatic gain control circuit (AGC) associated with the output transducer. Other feedback methods may also be employed. AGC circuit 61 attempts to maintain a constant audio output level and sends a feedback signal along line 63 to oscillator 39. In a situation where the conduit 21 of FIG. 1 is open, there is specific loading on the output transducer 35 and a specific amount of AGC feedback. On the other hand, when the open end of the conduit makes contact with a liquid boundary, closing the conduit, the amount of energy necessary to maintain the same output level is changed, thereby requiring a different amount of AGC feedback to oscillator 39. The level of feedback may be transmitted to detector 65 and the amplitude of feedback interpreted as acoustic impedance, Z. Changes in amplitude, wavelength, frequency or phase are all related to acoustic impedance and the term "acoustic impedance" in its broadest sense is intended to encompass such changes in amplitude or wavelength or frequency or phase. The output signal taken along line 67 then indicates whether the conduit is open, partially open, as when a tip is in place or closed. This signal may be fed to a signal correction circuit for determining conduit conditions.

With reference to FIG. 3A, an acoustic transducer 71, such as a speaker, is shown to be driven by a sine wave oscillator 73 which feeds an output signal along line 75 to an audio amplifier 77 which in turn drives the output transducer 71. The oscillator and output transducer together form a pressure wave transmitter means. The oscillator 73 may be any of the well known types of oscillators which produces a continuous sine wave signal at a desired frequency. (About 50 hertz in this example.) This frequency is preferred for noise considerations, but other frequencies may also be used, including those frequencies having wavelengths which are shorter than the length of the conduit. However, if very short wavelengths are used, i.e. much smaller than the length of the conduit, it may become more difficult to distinguish between open, partially open and closed conduit end conditions. For this reason, a frequency of 50 hertz, having a wavelength of several meters is preferred because the length of the conduit is typically only a few centimeters, usually less than 20 centimeters.

A typical oscillator may be formed from an operational amplifier 74 with feedback components 76. A typical detector circuit is shown in FIG. 3B for use in the situation where a separate detector is employed. A microphone 81 picks up a pressure wave from a tube leading to a conduit where pressure waves have been introduced by the transducer of FIG. 3A. The microphone is a miniature microphone having an output along line 83 which is connected to a filtering network, typically comprising resistors 84 and capacitors 86. The filtered signal is transmitted to an amplifier 85 where the signal level is increased and then transmitted along line 87 to a rectifier network within the block 89. The rectifier network includes diodes 82, resistors 88 and operational amplifiers 90. The function of the rectifier network is to convert the sine waves to a DC level which is transmitted along line 91 to a level comparator 93. Here a reference level 95 is measured with respect to the DC level from rectifier network 89. Comparator 93 is able to signal along line 97 whether the signal received by microphone 81 is above or below a certain level set on the threshold line 95. The threshold line may be established by calibration and corresponds to a level above or below which there is a change in the open, partially open or closed condition of the conduit.

Two threshold levels are established in threshold line 95 by transistor 92. An input terminal 94 connected to the base of the transistor 92 is set either low, logic zero, or high, logic one, depending upon the operation being performed. If a tip-on/off detection operation is being performed, a logic one is applied to terminal 94 causing the output of driver transistor 92 to be at the millivolt level, nominally 570 millivolts into comparator 93 along line 95. In FIG. 4A, the non rectified tip-off signal is seen to have a maximum amplitude of between 300 and 400 millivolts, well below the threshold $V_T$ and hence the comparator output will be low for a no-tip condition. In a situation where a tip is supposed to be in place, but a no-tip condition is detected, an alarm 100 is sounded or the entire apparatus is shut down until the cause of the condition is determined. For example, using simple dual input gate logic circuit 99 shown in FIG. 3C, if a tip-on state is applied to one input 94, representing a commanded condition of the apparatus, and a no-tip state is detected at the, other input 97 at a time when the tip is supposed to be there, the alarm 100 or motor shut down is initiated via shut down circuit 103 using alarm signal 101 and motor control signal 102 to generate command signal 60. From FIG. 4B, it will be seen that the signal from the rectified microphone signal with the tip attached is between 700 and 1100 millivolts, well above the 570 millivolt threshold and so the output of comparator 93 will be high. A similar alarm or shut down condition may be implemented if a tip is in place when the commanded condition is tip off. A tip-off condition is usually implemented by a tip ejector found on almost all automated pipettes. Once the tip-on or tip-off determination has been made, the next determination is whether the conduit is open or blocked. For this determination, a logic zero is now applied to terminal 94, causing less conduction in the transistor 92 and less of a voltage drop across load resistor 94. If the nominal voltage at power supply terminal 96 is on the order of plus five volts and the value in bias resistors 98a and 98b is 10Kohms, the threshold voltage along line 95 is now about 2.5 volts. When the non-rectified microphone signal arriving along line 91 is in the range of 4 to 5 volts, as indicated in FIG. 4C, the output of comparator 93 is high. When the signal level is below the threshold voltage, the comparator output is low. A high output indicates that the tip is blocked and that liquid level contact has been made.

A low threshold voltage is used to measure tip on or off conditions because the change in acoustic impedance at the microphone due to constriction of the conduit is relatively small but distinctive. On the other hand a higher threshold voltage is used to measure conduit open or closed conditions because the change in acoustic impedance at the microphone due to blockage of the conduit is relatively large. This dual threshold approach to acoustic wave measurements in conduits has not been recognized in the prior art. Output line 97 is connected to a signal correlation circuit as described with reference to FIG. 1. When microphone 81 picks up a signal which causes the rectifier to produce in output different from the preexisting tip on or tip off condition on the one hand, or conduit open or closed condition, on the other hand, the comparator 93 switches states and indicates a change in amplitude of the received signal, i.e. a change in acoustic impedance of the conduit. Instead of providing a rectifier 89, a circuit measuring changes in have phase could have been substituted since the closing of the conduit presents a phase shift in the received waves which have been reflected from the closed end. As a general rule, changes in amplitude are easier to measure than phase changes, but in noisy environments, a phase change may be more accurate. The microphone 81 and detector, such as rectifier 89 and comparator 93, form a pressure wave receiver means.

The output transducer has been described as a speaker, but other acoustic transducers, such as piezoelectric crystals or a piston displacement means may also be used. It is possible to fashion the conduit end from a piezoelectric material such as barium titanate or piezoelectric KYNAR, a trademark of Pennwalt Corporation, to provide a driving signal. Another means of providing the driving signal is to fabricate the displacement plunger 27 in FIG. 1 out of nickel or another suitable ferromagnetic material which is driven magnetostrictively. Such a device would produce pressure waves similar to the ones obtained from a miniature speaker. In the present invention, since the conduit may be a pipette, pipette tips which form the open end of the conduit are readily disposable after a liquid handling operation so as to avoid contamination. For this purpose, it is preferable to use a miniature speaker and microphone as the pressure wave transmitter and receiver.

Previously, relative height of a liquid level has been described as the measurement of interest. However, absolute height may also be found by placing a container of liquid on a reference surface, such as reference surface 13 in FIG. 1. The reference surface has a known vertical position, while the liquid boundary layer 17 has an unknown position. Pressure waves are directed down the movable open-ended conduit 21, while the conduit whose tip presence has been confirmed and whose starting position is known is slowly moved toward the liquid boundary by known amounts. Pressure waves are generated in the conduit by a pressure wave transmitter, so that large changes in acoustic impedance in the conduit may be measured. Acoustic impedance is monitored as the conduit is moved toward the liquid boundary layer. When there is a change in acoustic impedance, indicative of contact with the liquid boundary layer, the position of the tip is recorded relative to the reference surface. The absolute height of the liquid boundary may be computed by simple subtraction.

I claim:

1. Pipette apparatus for determining tip on and off conditions comprising, an open-ended conduit facing a liquid boundary of a liquid body, a tip engageable with said open-ended conduit, said tip partially constricting the open end of said open-ended conduit when engaged therewith, means for moving the partially constricted open-ended conduit toward and away from said liquid boundary, the tip being blocked when in contact with the liquid boundary, pressure wave generating means directing pressure waves into said conduit for establishing acoustic impedance therein, and detector means for detecting acoustic impedance levels for an open-ended condition, an open-ended but constricted condition, and a blocked condition.

2. The apparatus of claim 1 wherein said detector means comprises a variable threshold means for establishing a first threshold used in measuring a tip on and off condition and for establishing a second threshold used in measuring a blocked conduit condition.

3. The apparatus of claim 2 wherein said detector means further comprises a comparator having a reference level line having a switch means connected thereto for applying a first voltage as said first threshold when measuring a tip on and off condition, and applying a second voltage as said second threshold when measuring a blocked and unblocked conduit condition.

4. The apparatus of claim 3 wherein said first voltage is less than one volt and said second voltage in more that one volt.

5. The apparatus of claim 1 comprising an alarm which is activated after a tip on commanded condition is applied and no pipette tip is detected by said detector means.

6. The apparatus of claim 5 wherein said alarm means shuts down said means for moving the conduit.

7. The apparatus of claim 1 comprising an alarm means which is activated after a tip off commanded condition is applied and a tip is detected by said detector means.

8. The apparatus of claim 7 wherein said alarm means shuts down said means for moving the conduit.

9. Pipette apparatus for determining tip on and off conditions comprising, a movable housing holding a pipette body having an open-ended conduit within the body and a plunger closing an end of the conduit distal to the open end, said open-ended conduit facing a liquid boundary of a liquid body, a tip engageable with said open-ended conduit, said tip partially constricting the open end of said open-ended conduit when engaged therewith, motor means for moving said housing towards and away from said liquid boundary to an extent whereby the partially constricted open end of said open-ended conduit comes into contact with said liquid boundary, the tip being blocked by the liquid boundary, speaker means mounted within the housing directing pressure waves into said conduit for establishing acoustic impedance therein, and detector means for detecting acoustic impedance levels for an open-ended condition, an open-ended but constricted condition and a blocked condition.

10. The apparatus of claim 9 wherein said detector means comprises a variable threshold means for establishing a first threshold used in measuring a tip on and off condition and for establishing a second threshold used in measuring a blocked conduit condition.

11. The apparatus of claim 10 wherein said detector means further comprises a comparator having a reference level line having a switch means connected thereto for applying a first voltage as said first threshold when measuring a tip on and off condition, and applying a second voltage as said second threshold when measuring a blocked and unblocked conduit condition.

12. The apparatus of claim 11 wherein said first voltage is less than one volt and said second voltage is more than one volt.

13. The apparatus of claim 9 comprising an alarm means which is activated after a tip on commanded condition is applied and no tip is detected by said detector means.

14. The apparatus of claim 13 wherein said alarm means shuts down said motor means.

15. The apparatus of claim 9 comprising an alarm means which is activated after a tip off commanded condition is applied; and a tip is detected by said detector means.

16. The apparatus of claim 15 wherein said alarm means shuts down said motor means.

* * * * *